United States Patent
Inoue et al.

(10) Patent No.: US 7,094,203 B2
(45) Date of Patent: Aug. 22, 2006

(54) MEDICAL IMAGING APPARATUS FOR DETECTION OF GAMMA RAYS AND REFLECTED ULTRASONIC WAVES

(75) Inventors: Tomio Inoue, Takasaki (JP); Tadashi Ito, Kiryu (JP); Masao Jimbo, Otawara (JP); Takeshi Sasaki, Isesaki (JP); Shuji Tsuchiya, Fujisawa (JP); Kenzo Eguchi, Machida (JP); Hao Wei, Ichikawa (JP); Katsuroh Ohwadano, Shinagawa-ku (JP); Hideki Ryuo, Fujisawa (JP)

(73) Assignee: Anzai Medical Kabushiki Kaisha, Tokyo (JP)

( * ) Notice: Subject to any disclaimer, the term of this patent is extended or adjusted under 35 U.S.C. 154(b) by 564 days.

(21) Appl. No.: 10/175,950

(22) Filed: Jun. 21, 2002

(65) Prior Publication Data
US 2003/0004413 A1 Jan. 2, 2003

(30) Foreign Application Priority Data
Jun. 21, 2001 (JP) ............................. 2001-188113

(51) Int. Cl.
*A61B 8/00* (2006.01)
(52) U.S. Cl. ...................... 600/439; 600/436; 600/437; 600/459; 600/461; 600/471; 250/363.01; 250/363.02; 250/366; 250/369; 250/370.1; 250/397
(58) Field of Classification Search ................ 600/436, 600/439, 459, 461, 471, 105, 117, 118, 407, 600/437, 431, 411; 250/363.02, 397, 369, 250/370.09, 366, 371, 363.01, 370.1
See application file for complete search history.

(56) References Cited

U.S. PATENT DOCUMENTS

| | | | |
|---|---|---|---|
| 4,435,838 A | | 3/1984 | Gourlay |
| 5,014,708 A | * | 5/1991 | Hayashi et al. .............. 600/436 |
| 5,489,782 A | * | 2/1996 | Wernikoff .................... 250/369 |
| 5,742,060 A | * | 4/1998 | Ashburn ................ 250/370.09 |
| 5,786,597 A | * | 7/1998 | Lingren et al. ........ 250/370.09 |
| 5,873,828 A | * | 2/1999 | Fujio et al. .................. 600/439 |
| 6,212,423 B1 | | 4/2001 | Krakovitz |
| 6,429,431 B1 | * | 8/2002 | Wilk ...................... 250/363.02 |
| 6,583,420 B1 | * | 6/2003 | Nelson et al. .............. 250/397 |

FOREIGN PATENT DOCUMENTS

| | | |
|---|---|---|
| JP | 56-155808 | 11/1981 |
| JP | 57-069850 | 4/1982 |

(Continued)

OTHER PUBLICATIONS

English language summary included for JP 63-19582. This document was cited in a requested EPO Search Report, a copy of which is also attached.

(Continued)

*Primary Examiner*—Brian L. Casler
*Assistant Examiner*—Baisakhi Roy
(74) *Attorney, Agent, or Firm*—Paul A. Guss

(57) ABSTRACT

Gamma rays obtained from radioisotope administered to an examinee are detected by a gamma ray information-detecting unit so that a first tomographic image obtained therefrom is formed on a CRT. Further, a second tomographic image of the examinee detected by using an ultrasonic wave information-detecting unit juxtaposed with respect to the gamma ray information-detecting unit is formed while making the second tomographic image overlap on the first tomographic image. Thus, it is possible to obtain a tomographic image in which relative positional relationship of tissue is clear.

8 Claims, 14 Drawing Sheets

FOREIGN PATENT DOCUMENTS

| | | |
|---|---|---|
| JP | 57-077980 | 5/1982 |
| JP | 57-166145 | 10/1982 |
| JP | 63-19582 | 1/1988 |

OTHER PUBLICATIONS

S. Fujimura et al., "Coded Aperture Emission CT Using M-Array," Transactions of the Society of Instrument and Control Engineers, vol. 28, No. 4,426/432 (1992).

Tadashi Ito et al., "Three Dimensional Reconstruction of $^{99m}Tc$ Distribution by Using Coded Aperture CT," Instrument Department of the Society of Instrument and Control Engineers, 17th Sensing Forum (2000).

C.G. Daley et al., "Tomography by Linear-Aperture Nuclear-Image Data Inversion," 5th Annual Conference on Frontiers of Engineering and Computing in Health Care (Proceedings, pp. 16-19), IEEE Engineering in Medicine and Biology Society (1983).

* cited by examiner

MEDICAL IMAGING APPARATUS FOR DETECTION OF GAMMA RAYS AND REFLECTED ULTRASONIC WAVES

BACKGROUND OF THE INVENTION

1. Field of the Invention

The present invention relates to a medical imaging apparatus in which a gamma camera apparatus and an ultrasonic apparatus are integrated into one unit.

2. Description of the Related Art

An ultrasonic apparatus is used in the medical field, for example, in which an ultrasonic wave is emitted onto an examinee and a tomographic image of the examinee is obtained on the basis of a reflected wave therefrom. The ultrasonic apparatus generates the tomographic image based on a time difference required for the arrival of the reflected wave caused by a difference in acoustic impedance among respective tissues of the examinee. The ultrasonic apparatus is widely utilized since it is compact and excellent in portability and can recognize the cross-sectional shape of the tissue while keeping out of contact with the examinee.

However, it is impossible to recognize a living tissue having a high acoustic impedance, for example, the internal structure of a bone tissue. Further, the acoustic impedance is low in the blood and the lymph as compared with other living tissues. Therefore, it is also difficult to recognize a state of the blood and the lymph.

In the meantime, there have recently been developed gamma camera apparatus (Anger camera apparatus) for detecting gamma rays emitted from a radioisotope (RI) administered to an examinee with a plurality of detectors arranged in a plane and a scintillator, and constructing two-dimensional internal information of the examinee based on the detected gamma rays. When the gamma camera apparatus is used, it is possible to obtain a vivid image of a specified tissue which has absorbed the radioisotope.

One gamma camera apparatus that has been proposed has a coded aperture plate having a number of apertures defined therein according to given rules and disposed in front of a scintillator, and constructs three-dimensional internal information of an examinee based on the information obtained from the coded aperture plate. For details, reference should be made to "Coded Aperture Emission CT Using M-array", Transactions of the Society of Instrument and Control Engineers, Vol. 28, No. 4,426/432 (1992), and "Three dimensional reconstruction of $^{99m}$Tc distribution by using coded aperture CT", Instrument department of the Society of Instrument and Control Engineers, 17th sensing forum (2000).

When the gamma camera apparatus described above is used, it is possible to obtain information of the tissue where the radioisotope is distributed. However, a considerably skillful technique is required in order to recognize the arrangement relationship between the tissue and other tissues of the examinee.

SUMMARY OF THE INVENTION

A general object of the present invention is to provide a medical imaging apparatus which makes it possible to obtain an easily analyzable tomographic image of an examinee including a specified tissue of the examinee.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
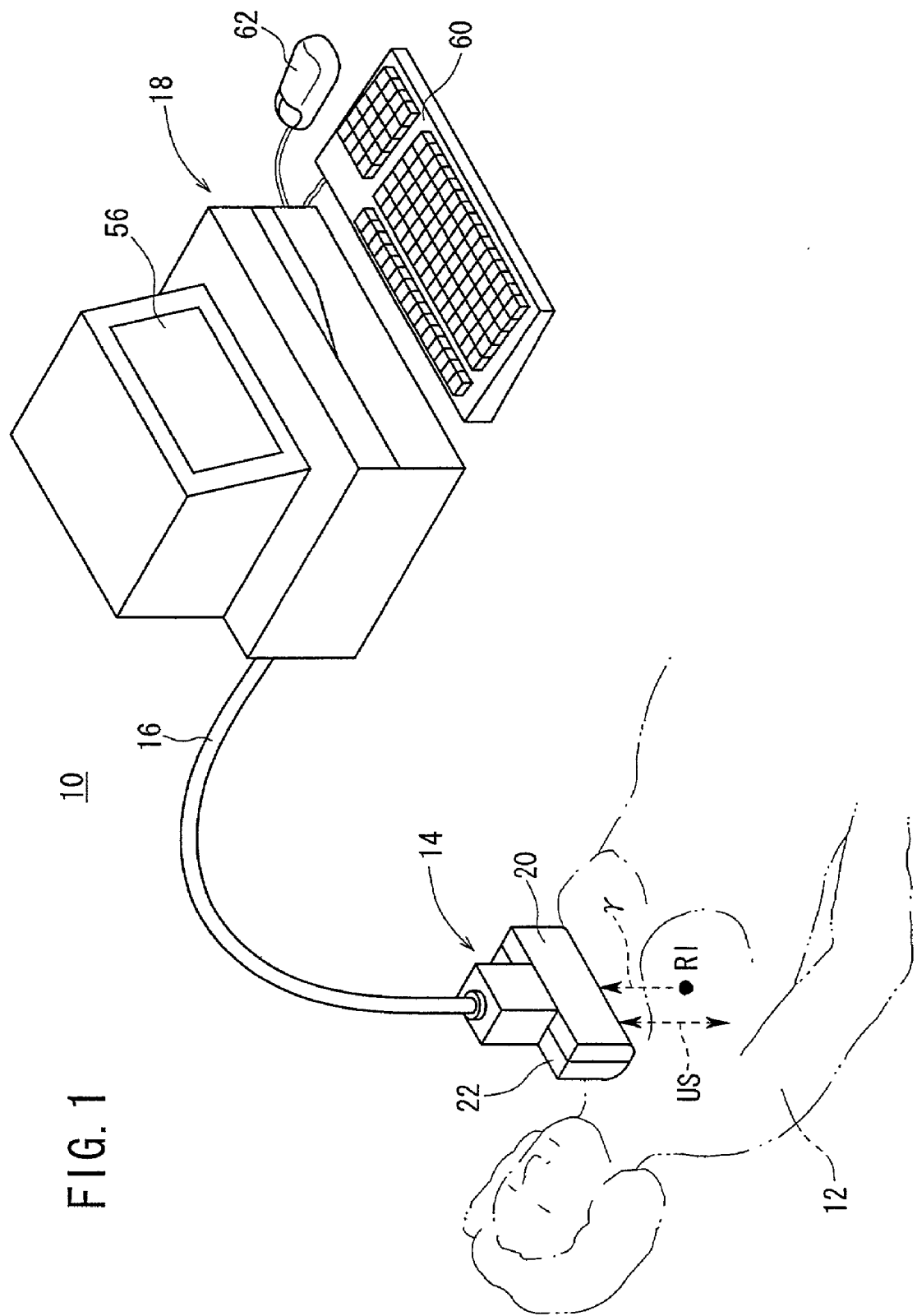
FIG. 1 shows an arrangement of a medical imaging apparatus according to an embodiment of the present invention.

FIG. 1 shows a medical imaging apparatus 10 according to an embodiment of the present invention. The medical imaging apparatus 10 basically comprises a probe 14 for incorporating tomographic image information of an examinee 12, and an information processing unit 18 (image-combining/displaying unit) connected to the probe 14 via a cable 16 for processing the incorporated tomographic image information.

The probe 14 includes a gamma ray information-detecting unit 20 for detecting gamma ray γ emitted from radioisotope RI in the examinee 12, and an ultrasonic wave information-detecting unit 22 for detecting information concerning reflected wave of ultrasonic wave US emitted to the examinee 12. In this arrangement, the gamma ray information-detecting unit 20 and the ultrasonic wave information-detecting unit 22 are juxtaposed adjacently to one another.

Figure 2:
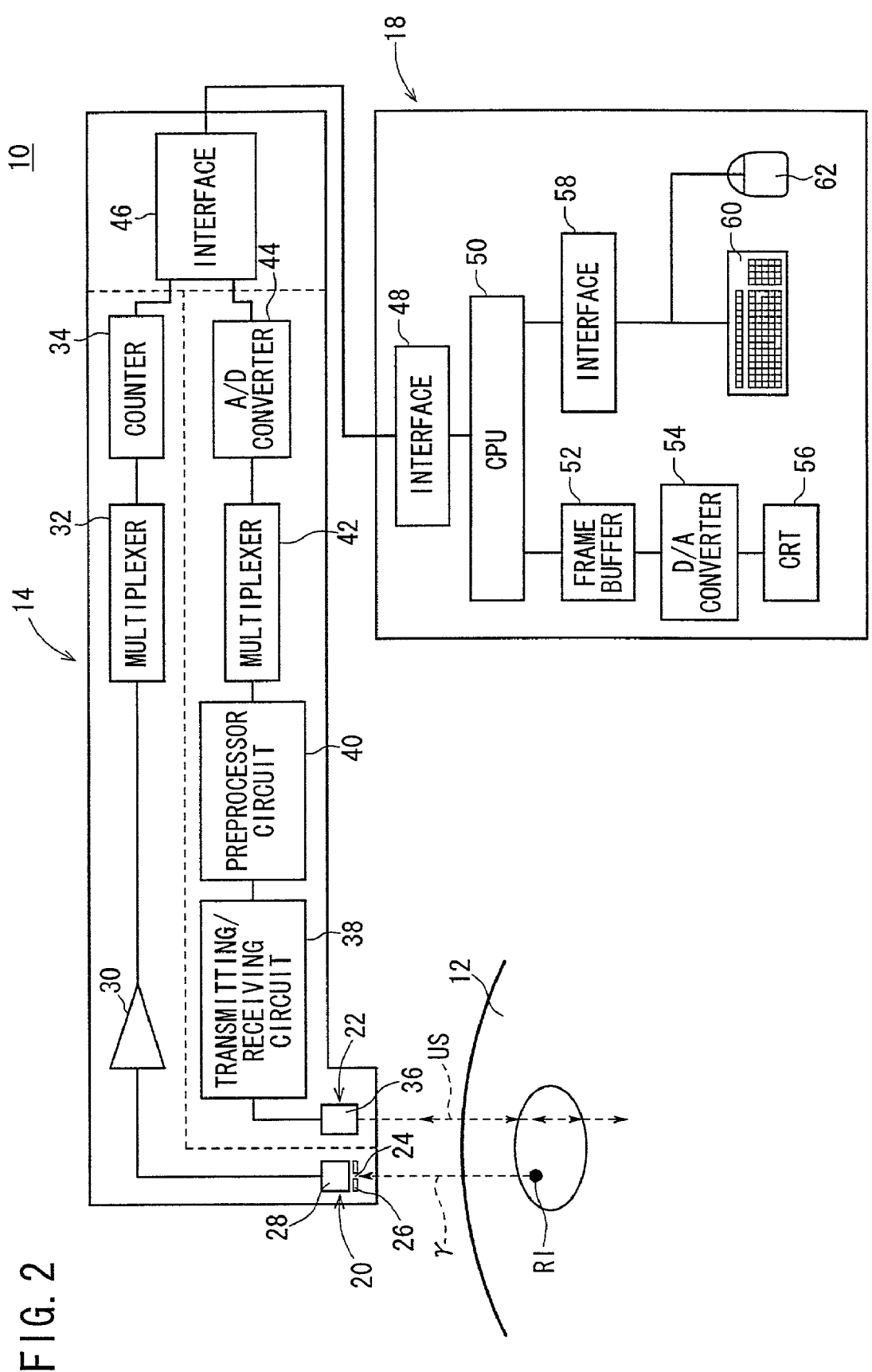
FIG. 2 is a block diagram illustrating a circuit structure of the medical imaging apparatus according to the embodiment of the present invention.
Figure 3:
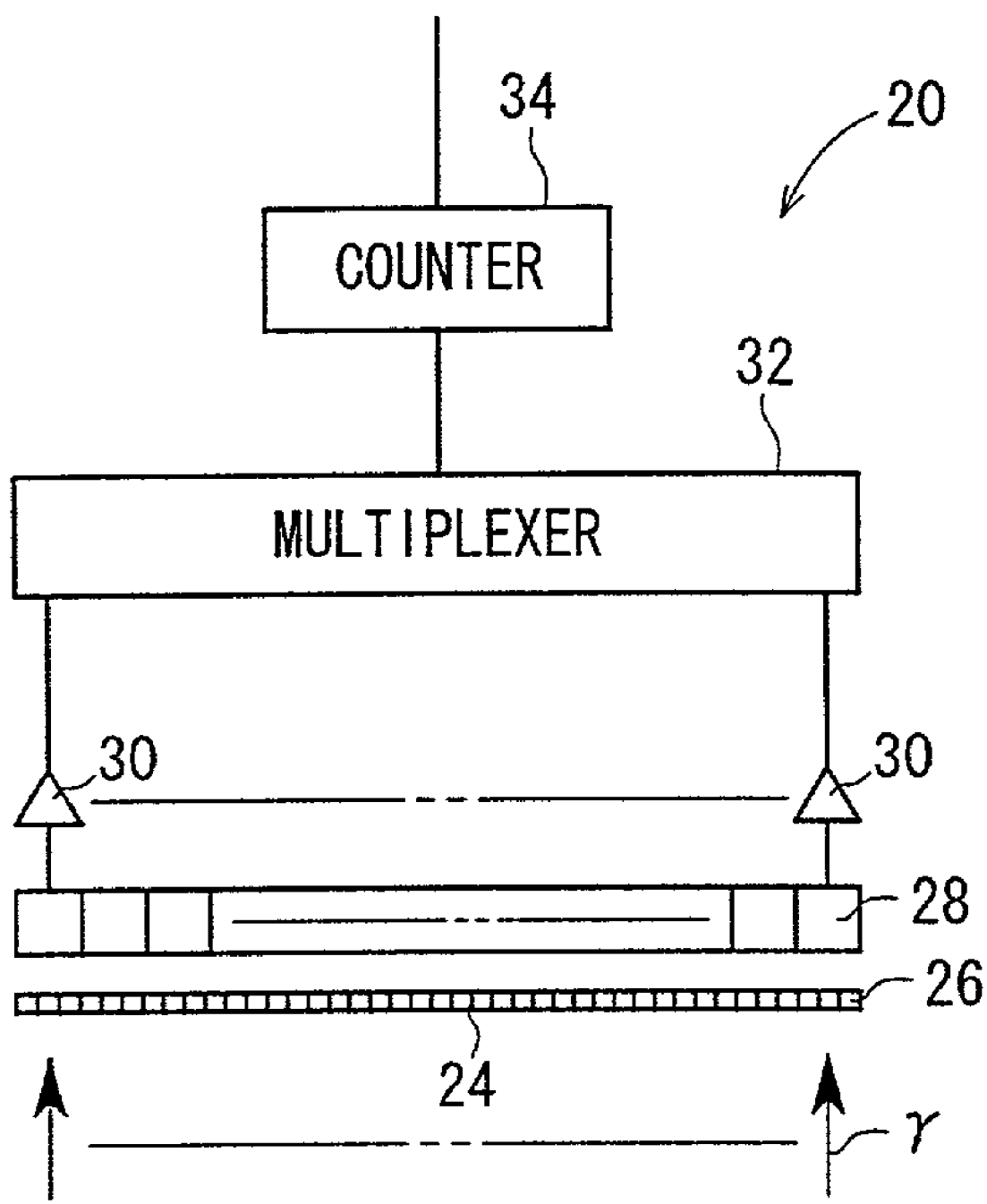
FIG. 3 is a block diagram illustrating a circuit structure of a gamma ray information-detecting unit according to the embodiment of the present invention.

FIG. 2 shows a block diagram illustrating a circuit structure of the medical imaging apparatus 10. The gamma ray information-detecting unit 20 of the probe 14 includes a collimator 26 (coded aperture plate) formed with a large number of pin hole-shaped apertures 24, and a plurality of semiconductor detecting elements 28 (gamma ray-detecting elements) for detecting the gamma ray γ passed through the collimator 26. As shown in FIG. 3, the apertures 24 of the collimator 26 and the plurality of semiconductor detecting elements 28 are arranged one-dimensionally. The intervals of the plurality of apertures 24 formed for the collimator 26 are set to a predetermined cycle pattern in conformity with the M sequence as a pseudo-random series. In this case, the auto-correlation function of the M sequence is close to the δ function, and the correlation function value is constant at those other than the peak. For example, CdTe and CdZnTe may be used for the semiconductor detecting element 28. Each of the semiconductor detecting elements 28 is connected to a multiplexer 32 via a signal amplifier 30. The multiplexer 32 successively switches the gamma ray detection signal supplied from each of the semiconductor detecting element 28, and it supplies the signal to the counter 34.

As for the intervals of the apertures 24, it is also possible to use those based on, for example, the Q sequence (square residue sequence), the Gold sequence, and the Walsh code, instead of the M sequence, as long as those are based on the binary pseudo-random sequence.

Figure 4:
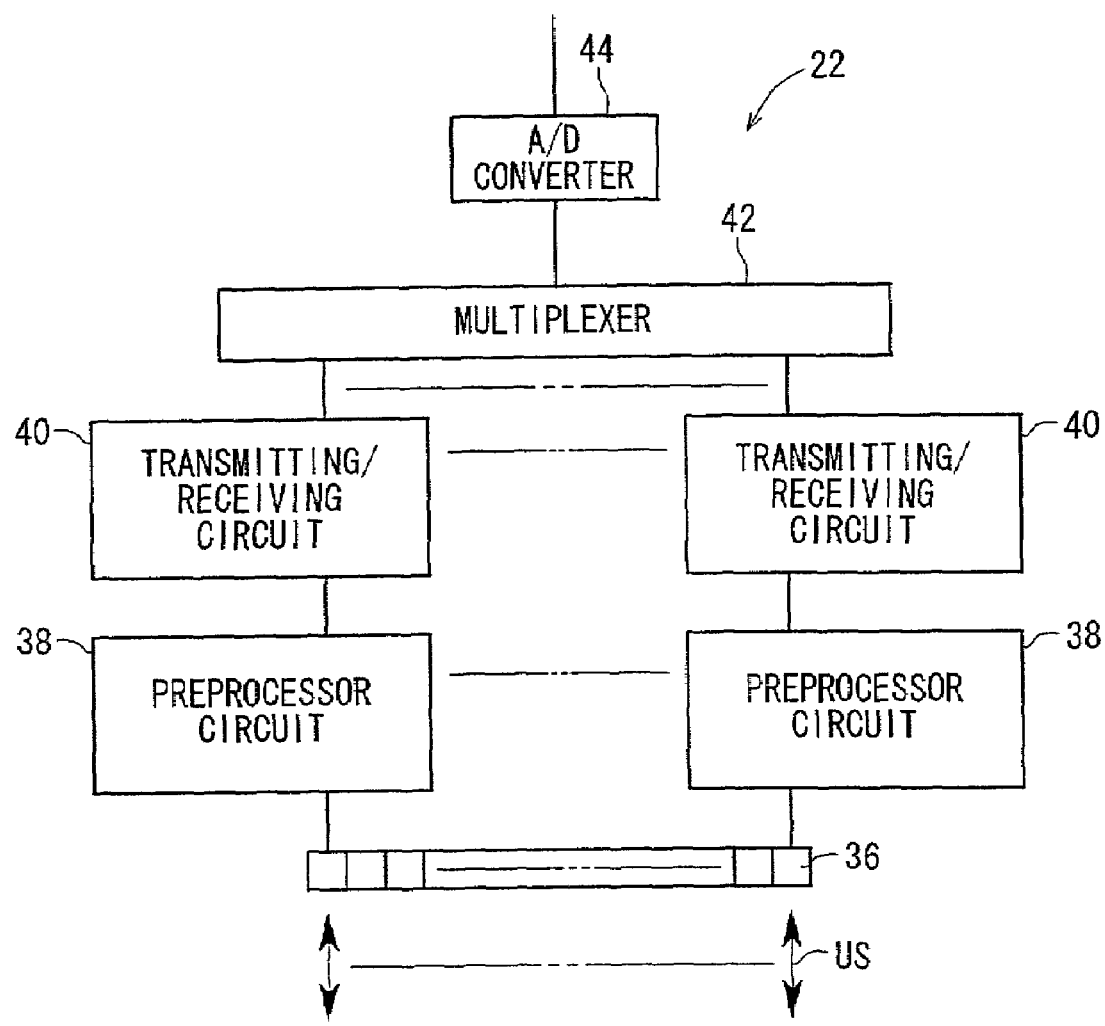
FIG. 4 is a block diagram illustrating a circuit structure of an ultrasonic wave information-detecting unit according to the embodiment of the present invention.

The ultrasonic wave information-detecting unit 22 of the probe 14 includes a plurality of minute vibrators 36 (ultrasonic wave-transmitting/receiving elements) comprising piezoelectric ceramics etc. for emitting the ultrasonic wave US and receiving the reflected wave of the ultrasonic wave US reflected by the examinee 12. The minute vibrators 36 are juxtaposed closely to the semiconductor detecting elements 28. As shown in FIG. 4, the minute vibrators 36 are arranged one-dimensionally. Each of the minute vibrators 36 is connected to a multiplexer 42 via a transmitting/receiving circuit 38 for transmitting/receiving the ultrasonic wave US and the reflected wave thereof, and a preprocessor circuit 40 for preprocessing the detection signal of the reflected wave. The multiplexer 42 successively switches the detection signal of the reflected wave supplied from each of the minute vibrators 36, and supplies the signal to an A/D converter 44.

The probe 14 is connected to the information processing unit 18 via an interface circuit 46. The information processing unit 18 is, for example, a personal computer. The information processing unit 18 includes a CPU 50 for processing the gamma ray detection signal and the reflected wave detection signal received from the probe 14 via the interface circuit 48 to construct a tomographic image of the examinee 12. A CRT 56 for displaying the tomographic image is connected to the CPU 50 via a frame buffer 52 and a D/A converter 54. A keyboard 60 and a mouse 62 for inputting desired operation data are connected to the CPU 50 via an interface circuit 58.

In this case, the probe 14 may also be constructed by joining a gamma ray information-detecting unit 20 and an ultrasonic wave information-detecting unit 22 which are formed independently, to be integrated into one unit.

Figure 5:
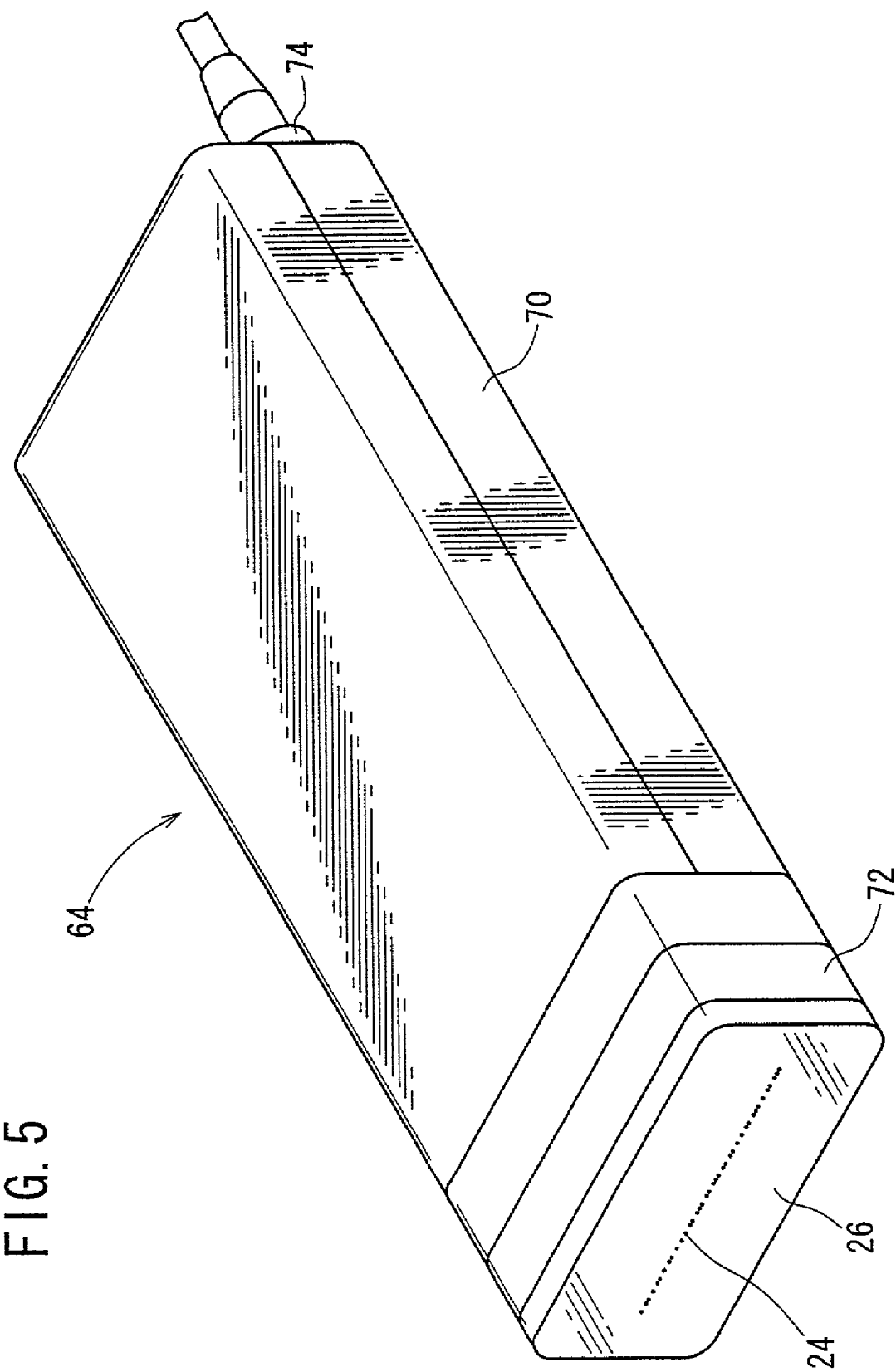
FIG. 5 shows an arrangement of a gamma ray information-detecting unit according to an embodiment of the present invention.
Figure 6:
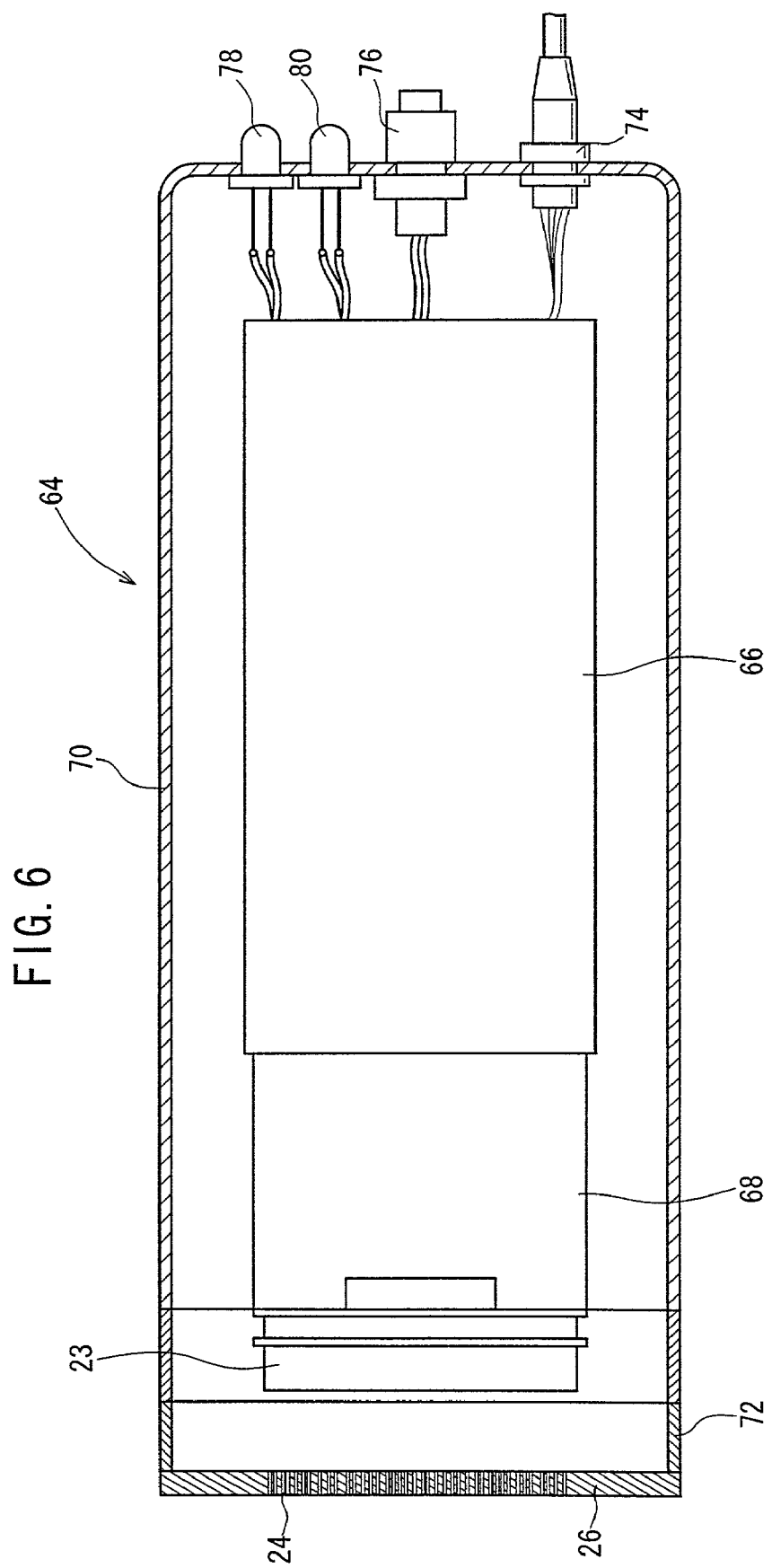
FIG. 6 is a lateral sectional view illustrating the gamma ray information-detecting unit shown in FIG. 5.
Figure 7:
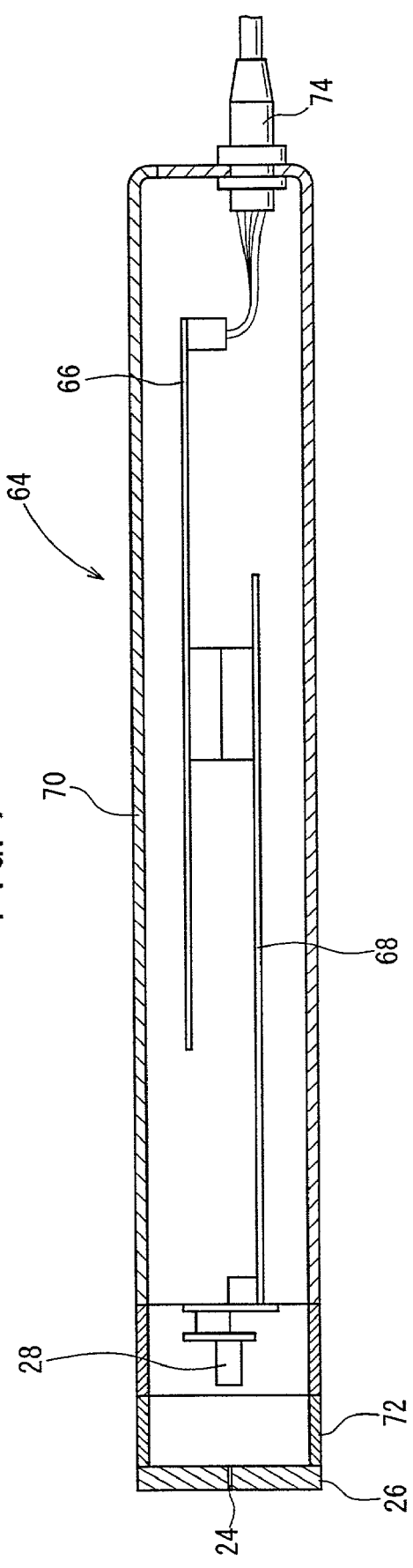
FIG. 7 is a longitudinal sectional view illustrating the gamma ray information-detecting unit shown in FIG. 5.

FIGS. 5 to 7 show a specified example of the gamma ray information-detecting unit 64 which is constructed independently. The gamma ray information-detecting unit 64 has a casing 70 in a rectangular shape containing circuit boards 66, 68 which carry a signal processing circuit including a signal amplifier 30 shown in FIG. 2, a multiplexer 32, a counter 34, and an interface circuit 46. The casing 70 also contains semiconductor detecting elements 28 connected to the circuit boards 66, 68. A collimator 26 is arranged at one end of the casing 70 with a spacer 72 intervening therebetween. The collimator 26 has a plurality of apertures 24 arranged in a direction parallel to the semiconductor detecting elements 28. At the other end of the casing 70, a connector 74 for connecting the gamma ray information-detecting unit 64 to the information processing unit 18 is arranged. A count start switch 76 for counting the gamma ray detection signal with the gamma ray information-detecting unit 64, indicator lamps 78, 80 for indicating the operation state of the gamma ray information-detecting unit 64, and other components are arranged in the vicinity of the connector 74. In the gamma ray information-detecting unit 64 constructed as described above, the spacing distance between the collimator 26 and the semiconductor detecting element 28 is adjustable by the spacer 72.

The medical imaging apparatus 10 according to the embodiment of the present invention is basically constructed as described above. Next, the operation, function, and effect of the medical imaging apparatus 10 will be explained.

At first, explanation will be made for the process in which the gamma rays γ emitted from the examinee 12 is counted by the gamma ray information-detecting unit 20 and processed by the information processing unit 18 to construct a first tomographic image.

Figure 8:
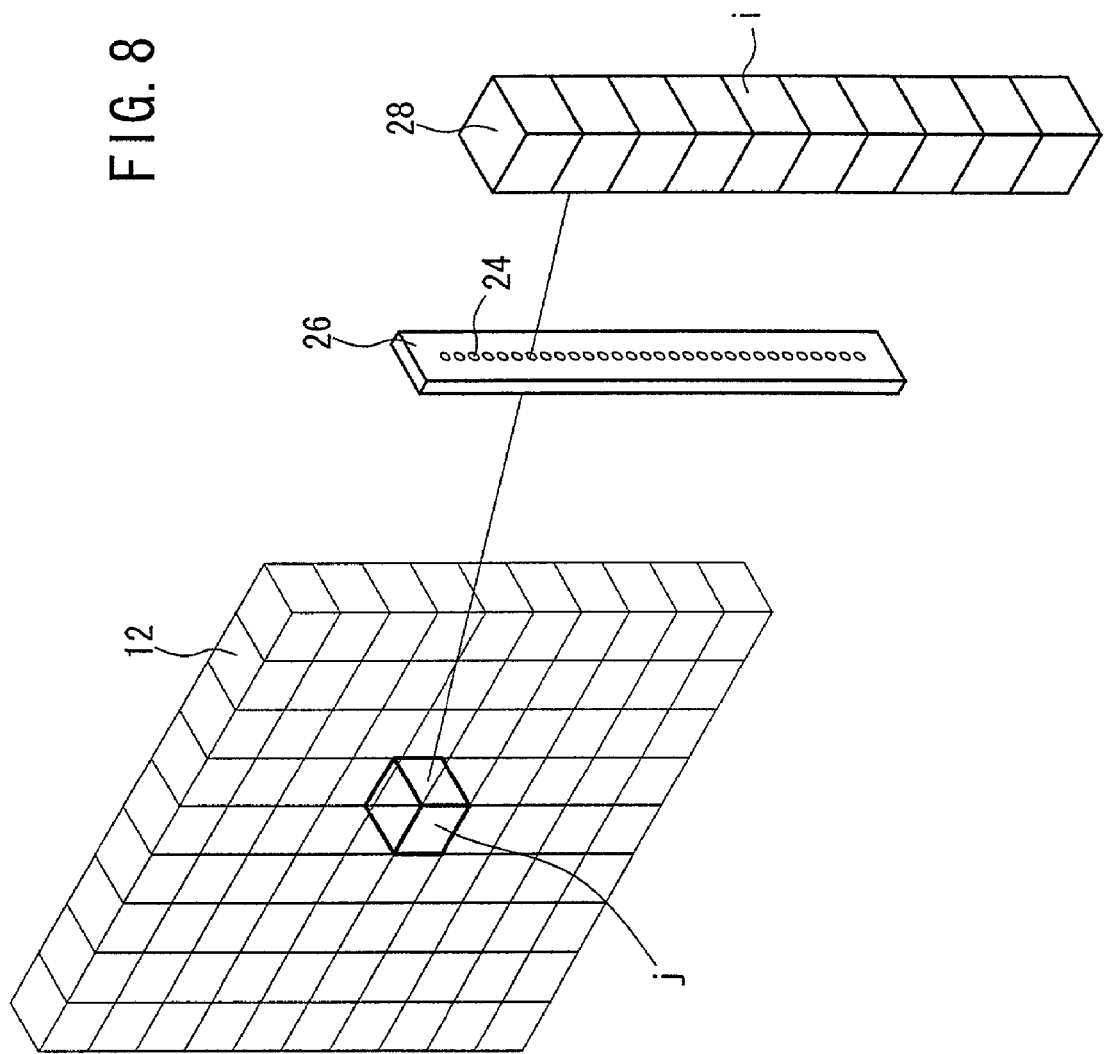
FIG. 8 explains the principle of construction of a tomographic image based on gamma ray information detected by the gamma ray information-detecting unit according to the embodiment of the present invention.

In a schematic illustration shown in FIG. 8, the examinee 12, in which the radiation source (radioisotope RI) for emitting the gamma rays γ may exist, is divided into n voxels for an arbitrary cross-sectional layer. One of the voxels is designated as j (j=1, 2, . . . , n). It is assumed that the number of elements of the semiconductor detecting elements 28 for detecting the gamma ray γ is m, and one of the elements is designated as i (i=1, 2, . . . , m).

It is also assumed that $S_j$ represents the expected value of the count of the gamma rays γ emitted by the jth voxel for a certain constant period of time, $P_i$ represents the expected value of the count of the gamma rays γ detected by the ith semiconductor detecting element 28 for a constant period of time, and $P^*_i$ represents a count of the actually detected gamma rays γ. Assuming that $f_{ij}$ represents the probability of detection of the gamma rays γ emitted from the jth voxel by the ith semiconductor detecting element 28, the following equation is satisfied:

$$P_i = \sum_{j=1}^{n} f_{ij} S_j \quad (i = 1, 2, \ldots, m) \tag{1}$$

The count of the gamma rays γ emitted from the radiation source is randomly varied in accordance with the Poisson's distribution. Therefore, the count detected by the ith semiconductor detecting element 28 is also randomly varied, and its expected value $P_i$ is given by the expression (1).

The probability $f_{ij}$ is geometrically determined by the positional relationship of the jth voxel, the ith semiconductor detecting element 28, and the aperture 24 of the collimator 26, and the M sequence as the arrangement pattern of the apertures 24. However, even under an ideal condition where the gamma rays γ are neither absorbed nor scattered, it is difficult to strictly determine the value of the probability $f_{ij}$ by calculation because the amount of calculation is large. Therefore, in the actual calculation, the probability $f_{ij}$ is approximately determined assuming that the radiation source distribution in the voxel is represented by a point radiation source placed at the center of the voxel.

That is, a path of the gamma rays γ emitted from the jth voxel and reaching the ith semiconductor detecting element 28 is of a conical shape whose vertex is positioned at the center of the jth voxel and the bottom at the ith semiconductor detecting element 28. If the vertex of the conical shape has a solid angle Ω and the ratio of the area of the apertures 24 to the area of the collimator 26 which is intersected by the conical shape (geometric-optical transmittance) is represented by τ, the probability $f_{ij}$ is given as:

$$f_{ij} = (\Omega/4\pi) \cdot \tau \quad (2)$$

When the semiconductor detecting element 28 is small compared with the voxel, a conical shape may be constructed which has a vertex positioned at the center of the semiconductor detecting element 28 and a bottom held in contact with the voxel. Accordingly, it is possible to determine the probability $f_{ij}$ more accurately from such a conical shape.

IF the distribution of the radiation source is represented by $S=(S_1, S_2, \ldots, S_n)$ and the count of the gamma rays γ is represented by $P^*=(P^*_1, P^*_2, \ldots, P^*_m)$, then a conditional probability (likelihood) Prob(P*|S) that the number of count P* is obtained under the condition that the distribution S is observed is represented by the following expression (3) using the expression of the Poisson distribution and the expression (1). In the expression (3), it is assumed that the symbol "^" indicates the exponentiation or power.

$$Prob(P^* \mid S) = \prod_{i=1}^{m} (P_i \wedge P_i^* / P_i^* !) \cdot \exp(-P_i) \quad (3)$$

The image reconstructing unit 18 asymptotically determines a radiation source distribution S where the conditional probability (likelihood) Prob(P*|S) according to the equation (3) has a maximum value.

Figure 9:
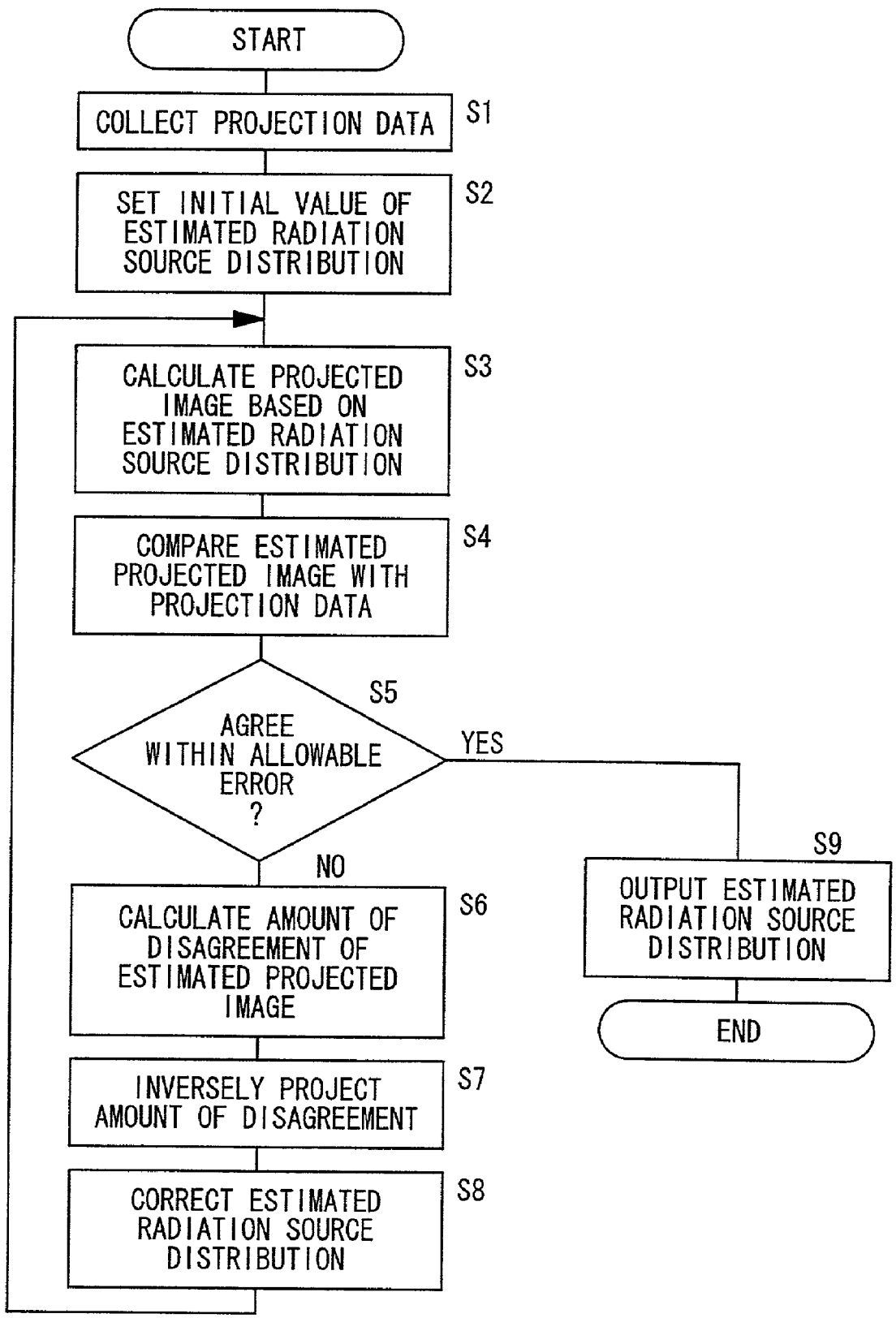
FIG. 9 is a process flow chart illustrating the construction of the tomographic image based on the gamma ray information detected by the gamma ray information-detecting unit according to the embodiment of the present invention.

FIG. 9 shows a flow chart of a specific process carried out by the information processing unit 18 for determining the radiation source distribution S using the expression (3).

At first, the gamma rays γ emitted from the radioisotope RI administrated into the examinee 12 are detected by the semiconductor detecting element 28 though the collimator 26. The signal is introduced into the counter 34 via the signal amplifier 30 and the multiplexer 32 to be the counted operation. The count signal is incorporated, and thus the count P* as projection data of the radiation source is collected (step S1). Subsequently, an initial value of the estimated radiation source a distribution S (step S2) is set, and then an expected value $P=(P_1, P_2, \ldots, P_m)$ as the estimated projected image of the radiation source is calculated (step S3). The initial value of the estimated radiation source distribution S can be set so as to have a uniform distribution, for example.

Subsequently, the expected value P determined as indicating the estimated projected image in step S3 and the count P* which represents the projection data collected in step S1 are compared with each other (step S4). It is then determined whether the expected value P and the count P* agree with each other within an allowable error (step S5). If the expected value P and the count P* do not agree with each other within the allowable error, an amount of the disagreement P*/P of the estimated projected image is calculated (step S6). The amount of disagreement P*/P is then inversely projected onto the examinee 12 (step S7). Thus, distribution S of the estimated radiation source is corrected (step S8).

The expected value P asymptotically approaches the count P* by repeatedly performing the processes of steps S3 to S8. If the expected value P and the count P* agree with each other within the allowable error in step S5, the distribution S of estimated radiation source at that time is outputted as the first tomographic image data for a desired cross-sectional surface of the examinee 12 to the frame buffer 52 (step S9).

Next, explanation will be made for the process of detecting the reflected wave of the ultrasonic wave US emitted to the examinee 12 by the ultrasonic wave information-detecting unit 22, and constructing the second tomographic image by processing the detection of the reflected image with the information processing unit 18.

A part of the ultrasonic wave US emitted from the minute vibrator 36 based on the driving operation of the transmitting/receiving circuit 38 is reflected by the tissue of the examinee 12. The reflected wave is detected by the minute vibrator 36 as a reflected wave detection signal. Each of the minute vibrators 36 transmits the detected reflected wave detection signal to the multiplexer 42 via the transmitting/receiving circuit 38 and the preprocessor circuit 40. The multiplexer 42 successively switches the reflected wave detection signal and transmits the signal to the information processing unit 18 via the A/D converter 44 and the interface circuit 46.

The information processing unit 18 calculates the position information of the tissue of the examinee 12 from the reflected wave detection signal detected by each of the minute vibrators 36 and outputs the information as the second tomographic image data to the frame buffer 52.

Figure 10:
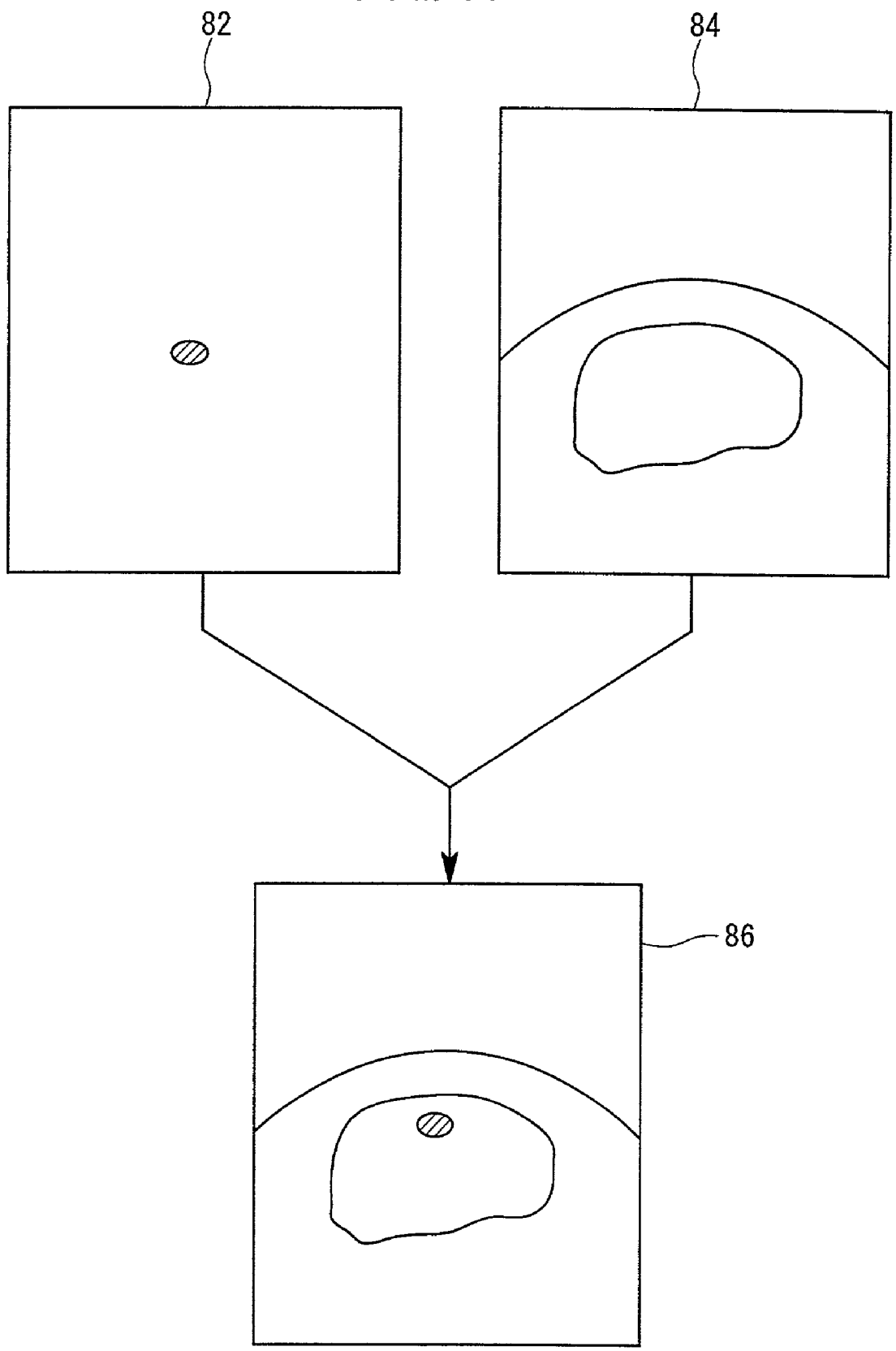
FIG. 10 illustrates combination of tomographic images by using the medical imaging apparatus according to the embodiment of the present invention.

Subsequently, as shown in FIG. 10, the CPU 50 of the information processing unit 18 superimposes, in the frame buffer 52, the first tomographic image 82 concerning the first tomographic image data obtained from the gamma ray information-detecting unit 20 on the second tomographic image 84 concerning the second tomographic image data obtained from the ultrasonic wave information-detecting unit 22 to generate a combined tomographic image 86. The combined tomographic image 86 is transmitted via the D/A converter 54 to the CRT 56 to be displayed thereon.

The first tomographic image 82 detected and obtained by the gamma ray information-detecting unit 20 is only the image of the portion where the radioisotope RI is distributed. On one hand, though it is possible to obtain the tomographic image of the tissue which has absorbed the radioisotope RI, the positional relationship with other tissues of the examinee 12 is unclear. On the other hand, the tomographic image of the tissue where the reflected wave exits can be obtained from the second tomographic image 84 detected by the ultrasonic wave information-detecting unit 22. Accordingly, a specified tissue absorbing the radioisotope RI can be easily confirmed in the tomographic image 86 obtained by superimposing the first tomographic image 82 on the second tomographic image 84 while the positional relationship with respect to the other tissues of the examinee 12 is clear. In this case, if the first tomographic image 82 and the second tomographic image 84 are displayed in different colors, respectively, it is possible to recognize and analyze the state of the tissue more clearly.

In the probe 14 shown in FIG. 1, the gamma ray information-detecting unit 20 and the ultrasonic wave information-detecting unit 22 are juxtaposed closely to one another. Accordingly, the first tomographic image 82 and the second tomographic image 84 are superimposed in the positional relationship corresponding to the spacing distance between the gamma ray information-detecting unit 20 and the ultrasonic wave information-detecting unit 22. Therefore, the tomographic image 86 of the tissue of the examinee 12 contains a certain positional shift within an allowable range.

Figure 11:
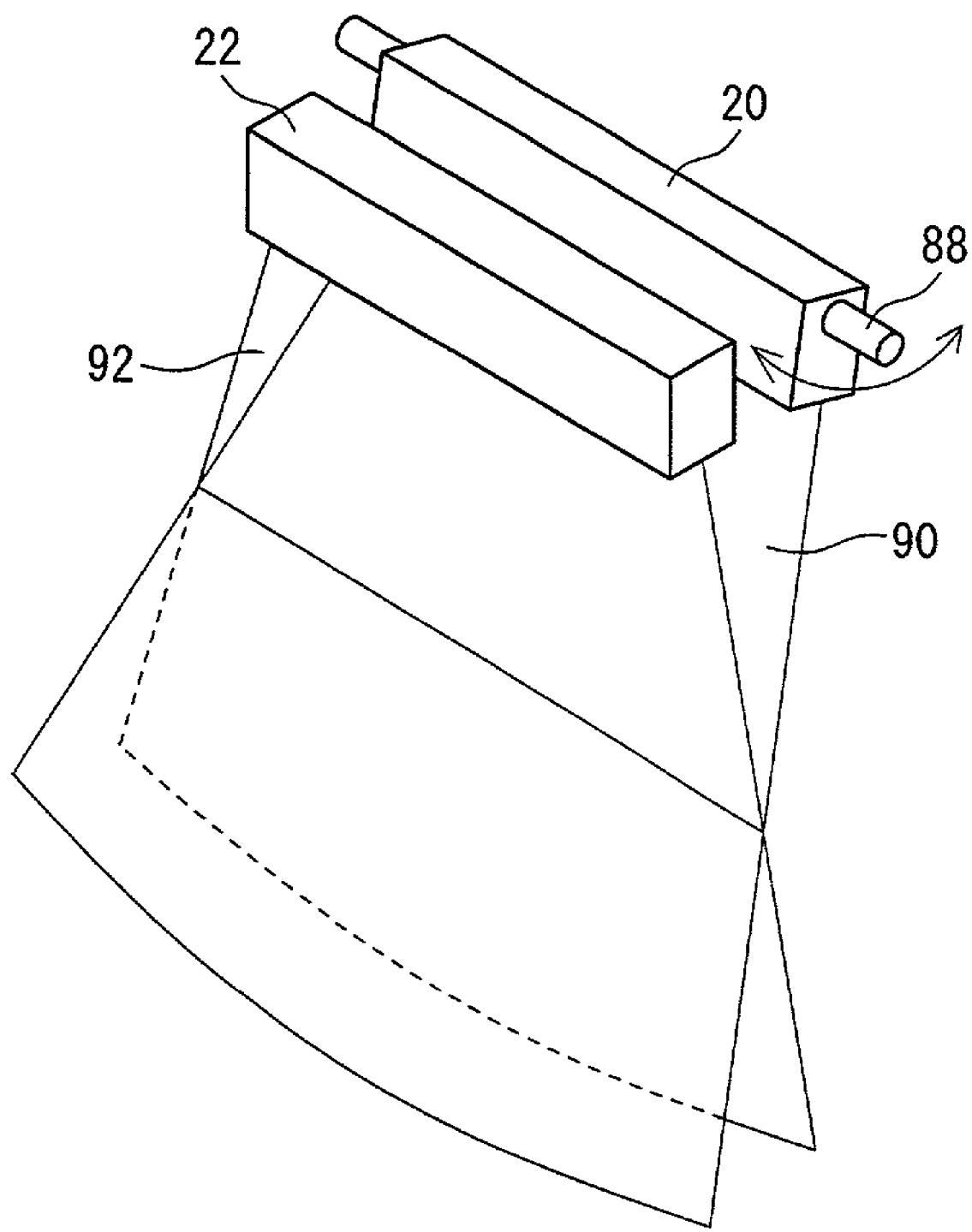
FIG. 11 illustrates another embodiment of the medical imaging apparatus according to the embodiment of the present invention.

By contrast, as shown in FIG. 11, the gamma ray information-detecting unit 20 may be designed to be rotatable by a predetermined angle about the center of a rotary shaft 88 arranged in the direction of arrangement of the semiconductor detecting elements 28, such that an imaging area 90 defined by the gamma ray information-detecting unit 20 may be set obliquely with respect to an imaging area 92 defined by the ultrasonic wave information-detecting unit 22. Thus, the imaging areas 90, 92 can intersect with each other. Therefore, the positions of the first tomographic image 82 and the second tomographic image 84 can agree with each other highly accurately in the vicinity of the intersection. It is a matter of course that the ultrasonic wave information-detecting unit 22 instead may be constructed to be rotatable with respect to the gamma ray information-detecting unit 20.

Figure 12:
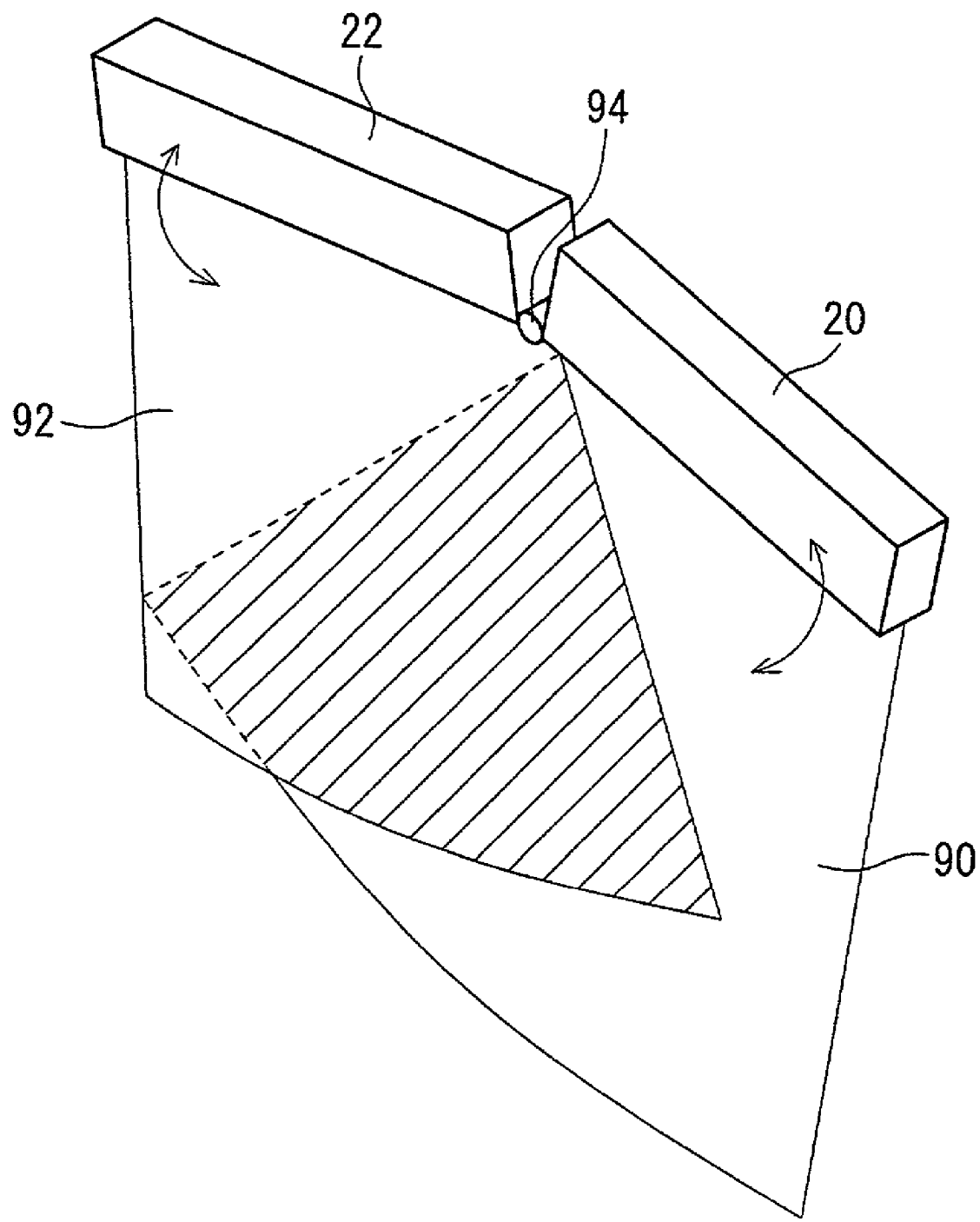
FIG. 12 illustrates another embodiment of the medical imaging apparatus according to the embodiment of the present invention.

In FIG. 12, the gamma ray information-detecting unit 20 and the ultrasonic wave information-detecting unit 22 are connected linearly with a hinge 94 so that those are rotatable with each other. In this arrangement, it is possible to obtain a tomographic image 86 where the positions of the first tomographic image 82 and the second tomographic image 84 agree with each other in a reliable manner at the site where the imaging areas 90, 92 are overlapped.

Figure 13:
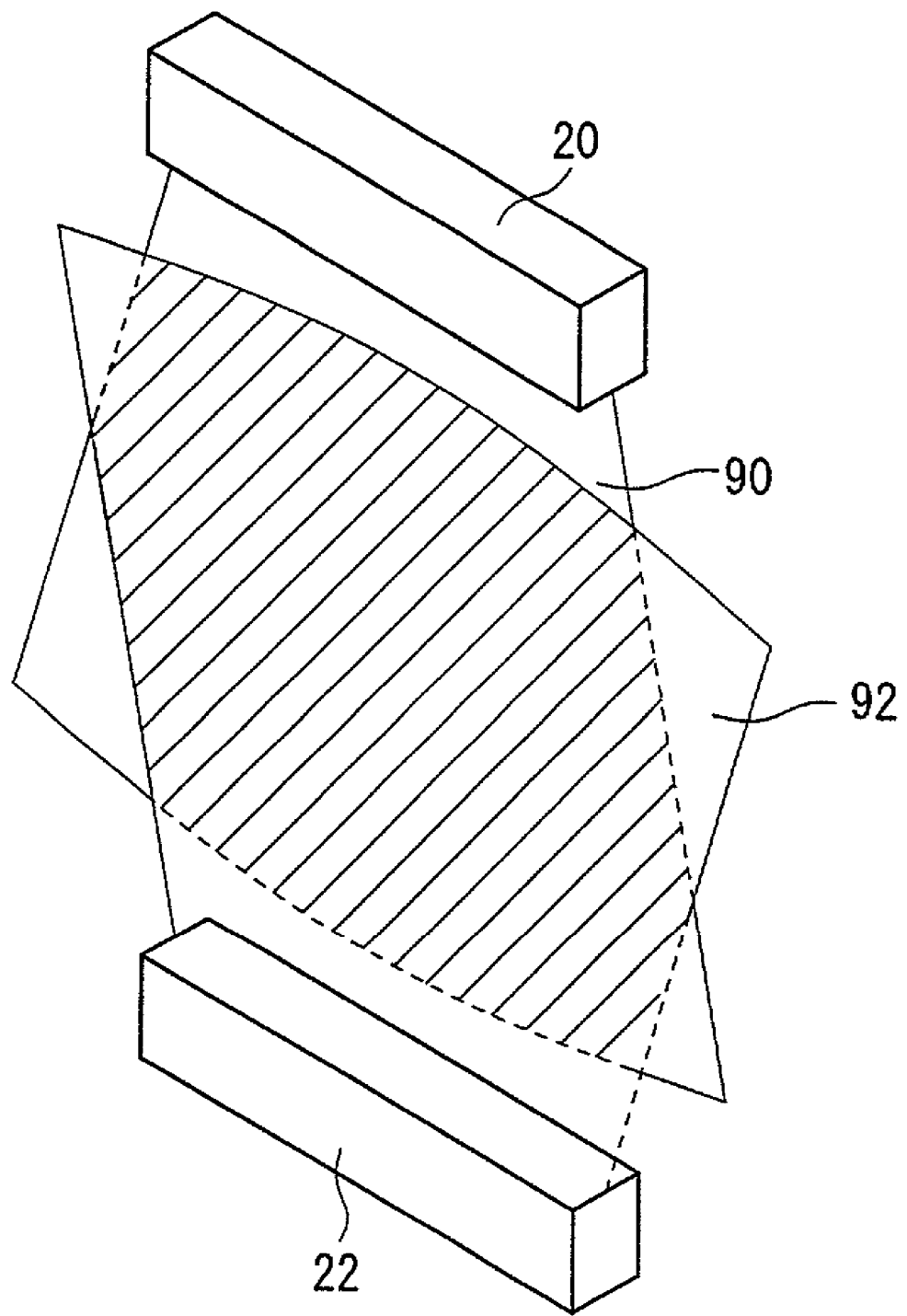
FIG. 13 illustrates another embodiment of the medical imaging apparatus according to the embodiment of the present invention.

In FIG. 13, the gamma ray information-detecting unit 20 and the ultrasonic wave information-detecting unit 22 are arranged opposingly. It is possible to obtain a tomographic image 86 in which the positions of the first tomographic image 82 and the second tomographic image 84 agree with each other, in the same manner as in the embodiment shown in FIG. 12.

Figure 14:
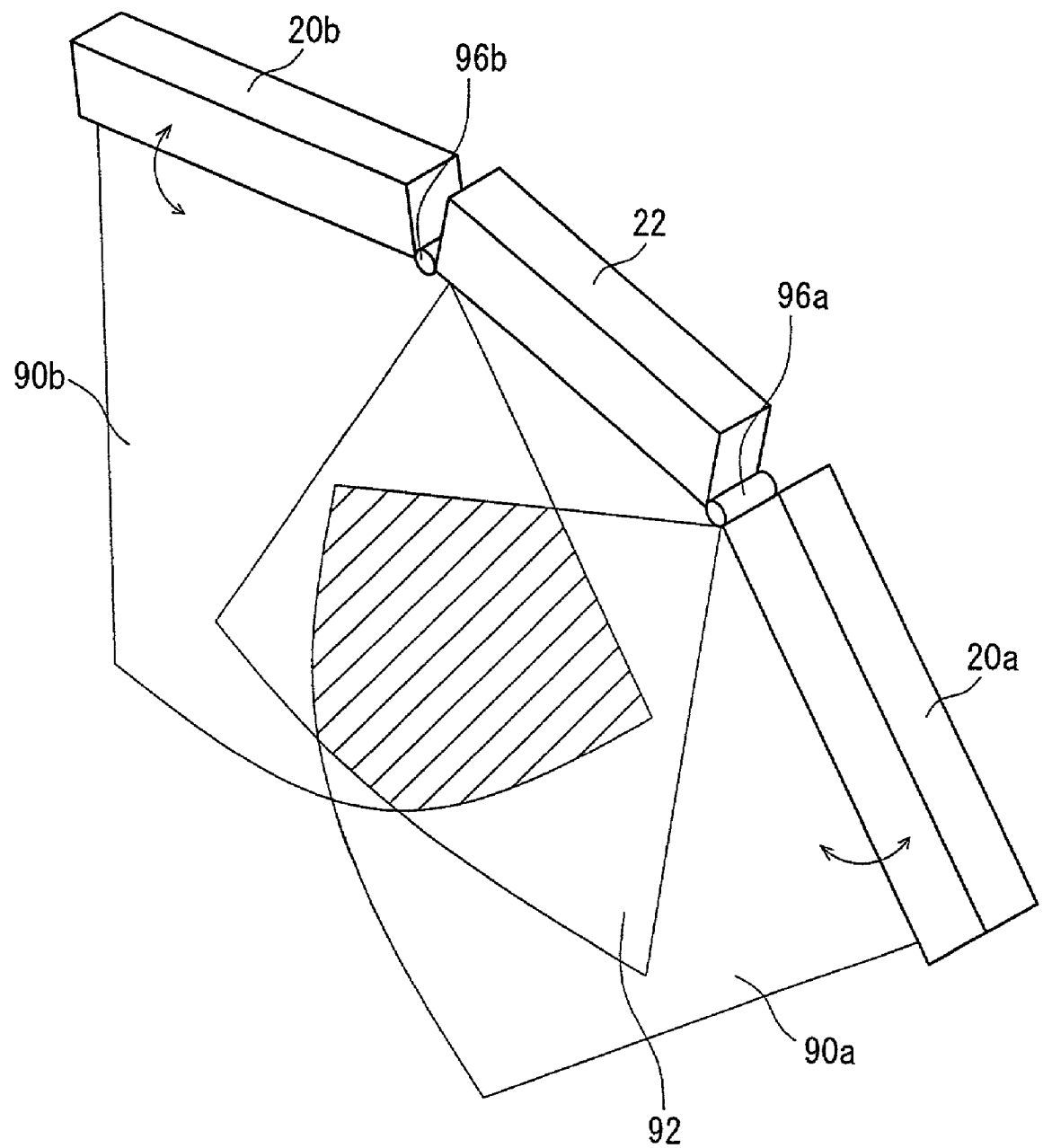
FIG. 14 illustrates another embodiment of the medical imaging apparatus according to the embodiment of the present invention.

In FIG. 14, two gamma ray information-detecting units 20a, 20b are connected linearly to both ends of the ultrasonic wave information-detecting unit 22 with hinges 96a, 96b. The respective gamma ray information-detecting units 20a, 20b are constructed to be rotatable with respect to the ultrasonic wave information-detecting unit 22. In this arrangement, the information on the first tomographic image 82 is obtained by each of the gamma ray information-detecting units 20a, 20b, so that it is possible to construct a more accurate first tomographic image 82. Therefore, it is possible to obtain a better tomographic image 86 at the site where the imaging areas 90a, 90b of the gamma ray information-detecting units 20a, 20b and the imaging area 92 of the ultrasonic wave information-detecting unit 22 are overlapped.

In the embodiments shown in FIGS. 11 to 14, the positions of the gamma ray information-detecting units 20, 20a, 20b and the ultrasonic wave information-detecting unit 22 can be mutually adjusted according to the position of the tissue in the examinee 12. Accordingly, a proper tomographic image of the tissue in the examinee 12 can be obtained.

Although certain preferred embodiments of the present invention have been shown and described in detail, it should be understood that various changes and modifications may be made therein without departing from the scope of the appended claims.

What is claimed is:

1. A medical imaging apparatus comprising:

a linear gamma ray information-detecting unit for detecting, at a position external to an examinee, gamma rays from a radioisotope administered to said examinee, to obtain a first tomographic image of said examinee from a distribution of said radioisotope;

a linear ultrasonic wave information-detecting unit for detecting, at a position external to said examinee, reflected waves caused by ultrasonic waves emitted to said examinee to obtain a second tomographic image of said examinee; and an image-combining/displaying unit for combining and displaying said first tomographic image and said second tomographic image, wherein said linear gamma ray information-detecting unit includes a plurality of gamma ray-detecting elements all of which are arranged one-dimensionally in a single linear array, and a coded aperture plate arranged between said examinee and said plurality of gamma ray-detecting elements, said coded aperture plate having a plurality of apertures all of which are arranged one-dimensionally in a single linear array, said linear gamma ray information-detecting unit having a planar imaging area wherein said gamma ray-detecting elements lie on the planar imaging area; and wherein said linear ultrasonic wave information-detecting unit includes a plurality of ultrasonic wave-transmitting/receiving elements all of which are arranged one-dimensionally in a single linear array, said linear ultrasonic wave information-detecting unit having a planar imaging area wherein said ultrasonic wave-transmitting/receiving elements lie on the planar imaging area.

2. The medical imaging apparatus according to claim 1, wherein said linear gamma ray information-detecting unit and said linear ultrasonic wave information-detecting unit are juxtaposed closely to one another.

3. The medical imaging apparatus according to claim 2, wherein one of said linear gamma ray information-detecting unit and said linear ultrasonic wave information-detecting unit is set obliquely with respect to another about a direction of arrangement of said gamma ray-detecting elements or said ultrasonic wave-transmitting/receiving elements in order to make said planar imaging area of said linear gamma ray information-detecting unit and said planar imaging area of said linear ultrasonic wave information-detecting unit overlap with one another.

4. The medical imaging apparatus according to claim 1, wherein said linear gamma ray information-detecting unit and said linear ultrasonic wave information-detecting unit are set such that a direction of arrangement of said gamma ray-detecting elements is oblique with respect to a direction of arrangement of said ultrasonic wave-transmitting/receiving elements in order to make said planar imaging area of said linear gamma ray information-detecting unit and said planar imaging area of said linear ultrasonic wave information-detecting unit overlap with one another.

5. The medical imaging apparatus according to claim 1, wherein said linear gamma ray information-detecting unit and said linear ultrasonic wave information-detecting unit are arranged opposingly in order to make said planar imaging area of said linear gamma ray information-detecting unit and said planar imaging area of said linear ultrasonic wave information-detecting unit overlap with one another.

6. The medical imaging apparatus according to claim 1, comprising a plurality of linear gamma ray information-detecting units, each having a different planar imaging area, wherein said planar imaging areas of each of said plurality of linear gamma ray information-detecting units overlap with one another.

7. The medical imaging apparatus according to claim 1, wherein mutual positional relationships between said linear gamma ray information-detecting unit and said linear ultrasonic wave information-detecting unit are adjustable.

8. The medical imaging apparatus according to claim 1, wherein said coded aperture plate comprises a plurality of apertures arranged linearly at intervals according to one of an M sequence, a Q sequence, a Gold sequence and a Walsh code.

* * * * *